United States Patent
Stachowiak

(10) Patent No.: US 6,878,858 B2
(45) Date of Patent: Apr. 12, 2005

(54) RODENT MODEL FOR PARKINSON'S DISEASE

(75) Inventor: Michal K. Stachowiak, East Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 362 days.

(21) Appl. No.: 10/216,986

(22) Filed: Aug. 12, 2002

(65) Prior Publication Data

US 2003/0033620 A1 Feb. 13, 2003

Related U.S. Application Data

(60) Provisional application No. 60/311,540, filed on Aug. 10, 2001.

(51) Int. Cl.[7] .................. A61K 67/00; A61K 49/00; A61K 31/70
(52) U.S. Cl. ................. 800/9; 800/8; 424/9.2; 514/44
(58) Field of Search .................. 800/8, 9; 424/9.2; 514/44

(56) References Cited

PUBLICATIONS

Peng et al. Novel Nuclear Signaling Pathway Mediates Activation of Fibroblast Growth Factor Receptor–2 Gene by Type 1 and Type 2 Angiotensin II Receptors. Molec. Biol. Cell. Feb. 2001, vol. 12, pp. 449–462.*

Ekesbo, et al., (–)–OSU 6162 Inhibits Levodopa–indicued Dyskinesias in a Monkey Model of Parkinson's Disease, NeuroReport 8, (1997), pp. 2567–2570.

Pearce, et al., Chronic L–DOPA Administration Induced Dyskinesias in the 1–Methyl–4–phenyl–1,2,3,6–Tetrahydropyridine–Treated Common Marmoset (*Callithrix jacchus*), Movement Disorders, vol. 10, No. 6, 1995, pp. 731–740.

Peng, et al., Novel Nuclear Signaling Pathway Mediates Activation of Fibroblast Growth Factor–2 Gene by Type 1 and Type 2 Angiotensin II Receptors, Molecular Biology of the Cell, vol. 12, Feb. 2000, pp. 449–462.

Belluardo, et al. *Comparative Localization of Fibroblast Growth Factor Receptor –1, –2, and –3 mRNAs in the Rat Brain: In Situ Hybridization Analysis*, The Journal of Comparative Neurology, 1997, vol. 379, No. 2, pp. 226–246.

Gonzalez, et al. *A Comprehensive Analysis of the Distribution of FGF–2 and FGFR1 in the Rat Brain*, Brain Research, 1995, vol. 701, No. 1–2, pp. 201–226.

Stachowiak, et al. *Nuclear Accumulation of Fibroblast Growth Factor Receptors is Regulated by Multiple Signals in Adrenal Medullary Cells*, Molecular Biology of the Cell, 1996, vol. 7, No. 8, pp. 1299–1317.

* cited by examiner

*Primary Examiner*—Deborah Crouch
(74) *Attorney, Agent, or Firm*—Hodgson Russ LLP

(57) ABSTRACT

The present invention provides an animal model for Parkinson's Disease and a method for generating such a model. The method comprises the steps of transfecting dopaminergic neurons in the substantia nigra with a dominant negative mutant of FGFR1 with deleted tyrosine kinase domain. The animals are characterized by a reduction in the number of tyrosine hydroxylase neurons in the SNc area.

15 Claims, 4 Drawing Sheets

RODENT MODEL FOR PARKINSON'S DISEASE

This application claims priority of U.S. provisional application No. 60/311,540, filed on Aug. 10, 2001, the disclosure of which is incorporated herein by reference.

This work was funded, in part, by Grant no. IBN 9896371 from the National Science Foundation. The government has certain rights in the invention.

FIELD OF THE INVENTION

This invention relates generally to animal models for neurodegenerative diseases and more particularly to an animal model for Parkinson's Disease. This invention also provides a method of producing animals which can serve as models for Parkinson's Disease and a method for screening potential therapeutic agents.

DESCRIPTION OF RELATED ART

Parkinson's disease (PD) is a progressive, degenerative neurologic disorder which usually occurs in late mid-life, and is the second most common neurodegenerative disorder, after Alzheimer's disease. PD predominantly affects dopaminergic neurons in the nigrastriatal system but also several other regions of the brain, and is clinically characterized by bradykinesia, tremor, and rigidity.

Bradykinesia, a slowness or "poverty" of movement, slows the pace of such routine activities as walking and eating, and also makes other movements more difficult. Tremor is a shakiness that generally affects limbs that are not otherwise in motion. For those PD patients diagnosed at a relatively young age, tremor is reported as the most disabling symptom. Older patients face their greatest challenge in walking or keeping their balance. Rigidity is caused by the inability of muscles to relax as opposing muscle groups contract, causing tension which can produce aches and pains in the back, neck, shoulders, temples, or chest.

Parkinson's Disease is typified by the deterioration of substantia nigra (SNc) dopamine (DA) neurons and a consequent decrease of striatal DA content. While a limited number of cases are associated with mutations in the synuclein or the parkin genes, the etiology of prevalent episodes of PD remains unknown. Neuronal damage and behavioral deficits similar to those found in PD are elicited in laboratory animals by highly oxidative DA and pyridine analogs which suggests that the disease in humans may be triggered by endogenous and/or environmental neurotoxins. These mechanisms may involve free radicals but could also involve an insufficient production of neurotrophic substances or a disruption of the metabolic pathways that support neuronal homeostasis.

To compensate for reduced dopamine, PD patients are administered L-DOPA. This reduces the severity of symptoms such as bradykinesia, muscular rigidity and trembling. However, chronic treatment with L-DOPA is reported to cause secondary effects such as dyskinesia. Other treatments for PD include administration of Deprenyl (selegiline), which if begun early in the disorder, can slow progression of the disease. Further, there is also evidence that "antioxidants" such as vitamin E and selenium may be of some benefit.

Recently, it has been observed that fibroblast growth factor-2 (FGF-2), when exposed to the striatum, (i) stimulates regeneration of DA projections from SN of mice rendered Parkinsonian by the neurotoxin 1 methyl-4-phenyl-1,2,3,6-tetrahyropyridine (MPTP) and (ii) increases cell survival. Neuroprotective actions of transplanted cells engineered to release a chimeric FGF-2 was also shown in striatum and SN. There exists evidence that the action of extracellularly added FGF-2 on DA neurons in the SN is indirect, and mediated via mesencephalic glia. However, SN DA neurons were shown to express the mRNA and FGF-2 protein, to transport FGF-2 and express fibroblast growth factor receptor-1 (FGFR1), suggesting an autocrine action of FGF-2. While FGF-2 is considered relevant for the DA neurons in SN, the mechanism of action of FGF-2 is not known yet.

The development of animal models for the study of PD has been slow. Previously, 6-OH dopamine and MPTP injected rodents have been used as animal models for PD (Pierce et al., 1995, Movement Disorders; 10, no.6, 731–740; Ekesbo et al., Neuroreport, 8:2567–2570). However, in these models, PD-like symptoms are observed rapidly after injection of 6-OH dopamine or MPTP unlike the gradual progression seen in PD patients. Accordingly, these models do not accurately represent the onset of PD in humans. In the absence of suitable animal model for PD, the mechanism of action of FGF-2 and other putative factors, remains unclear. The lack of an animal model has also hampered efforts to identify potential targets for novel therapeutic approaches to PD. Accordingly, there is a need in the field of Parkinson's Disease to develop animal models that mimic the symptoms in humans.

SUMMARY OF THE INVENTION

The present invention provides an animal model for Parkinson's Disease. The animal model is generated by administration of a mutant of fibroblast growth factor receptor-1 (FGFR1) with deleted tyrosine kinase (TK) domain into the SNc of animals using polyethyleneimine (PEI). This results in a reduction in the number of tyrosine hydroxylase (TH)-expressing neurons in the SNc. These animals can be used for studying the mechanisms underlying PD and to test potential therapeutic approaches to PD.

Thus an object of the present invention is to provide a non-human animal model for Parkinson's Disease.

Another object of the present invention is to provide a method for making a non-human animals for Parkinson's Disease.

Another object of the present invention is to provide an animal model for the screening of therapeutic agents for Parkinson's Disease.

Another object of the present invention is to provide a method for screening potential therapeutic agents for PD.

These and other objects of the present invention will become apparent from the description and the claims appended thereto.

DETAILED DESCRIPTION OF THE INVENTION

Figure 1:
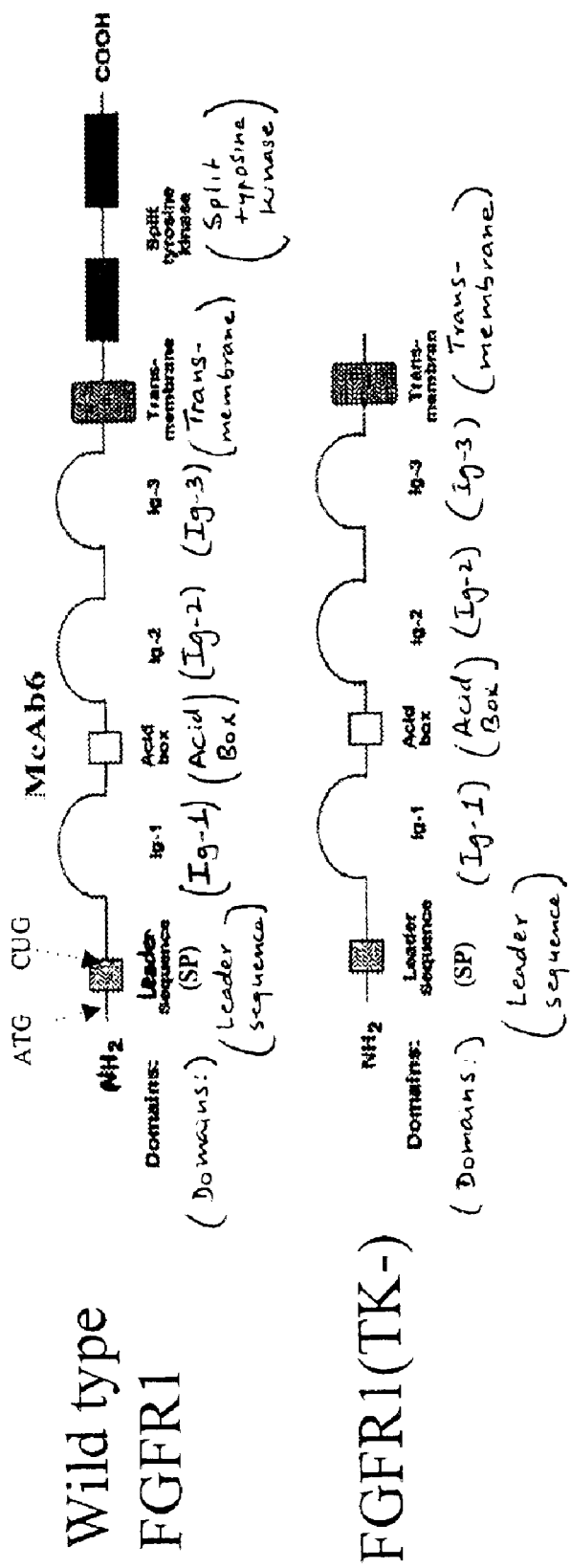
FIG. 1 is a schematic representation of the tyrosine kinase deficient mutant of FGFR1 and the wild type FGFR1.

The present invention is based on the surprising finding that injection of a TK negative mutant of FGFR1 into the substantia nigra region produces PD like symptoms. The symptoms are delayed for about 4 weeks from the time of injection. FGFs interact with high-affinity tyrosine kinase receptors (FGFR1–4) considered to mediate the known cellular responses to FGFs. Four genes encode the FGFR with multiple variants arising because of alternative splicing. Each gene encodes an extracellular N-terminal domain with 2–3 IgG loops containing the FGF binding region, single transmembrane domain (TM), and an intracellular split tyrosine kinase (TK) region. FGFR1 has C-terminal, TK-domain, and is associated with the intranuclear matric and the nucleoplasm, but not with the nuclear membrane. A schematic representation of FGFR1 is shown in FIG. 1.

The animals model of the present invention is produced by injection of a mutant of FGFR1 that lacks a TK site (hereinafter termed FGFR1(TK-)). This mutant is shown in FIG. 1. This mutant can be generated by deleting the FGFR1 sequence downstream from the transmembrane domain. An FGFR1(TK-) mutant was shown to be a dominant negative mutant meaning that it is a competitive antagonist in that it competes with the wild type protein for binding but is inactive (see Peng et al., Mol. Biol. Cell, 2001, 12:449–462, incorporated herein by reference). Thus, it forms non-phosphorylated, inactive dimers with FGFR.

The present invention discloses an animal model for Parkinson's Disease and a method of generating such a model. The method comprises the steps of transfecting a FGFR1[TK-] (FIG. 1) directly into the SNc of an animal using Polethyleneimine (PEI).

In the present invention, a non-human animal such as a rodent can be injected with the TK deficient mutant of FGFR1 to produce the model for PD. The rodent is typically a rat or a mouse. For injecting into the SN area, the animals can be placed on a stereotaxic apparatus. The location of the SN nucleus and injection of agents into the SN area is well within the purview of those skilled in the art. The TK deficient mutant DNA and PEI are generally mixed with pharmaceutically acceptable carriers such as glucose. The composition can be injected into the SNs of left, right or both hemispheres. Following recovery, the animals can be used at desired times. Generally, the animals start exhibiting PD symptoms after about 4 weeks. Animals can be sacrificed at desired time after surgery and an estimate of FGFR1 [TF-] induced lesions can be performed using standard techniques such as immunostaining of substantia nigra with tyrosine hydroxylase antibodies or by measuring dopamine content in dissected striatum using HPLC with electrochemical detection.

In one embodiment, a linear 22 kDa polyethyleneimine (PEI) is used for injection into adult rat brain. While not intending to be bound by any particular theory, it is considered that Polyethyleneimine (PEI) forms complexes with negatively charged DNA, which then enters the cell via endocytosis. Protonable amino nitrogen atoms make the PEI an effective proton "sponge" allowing for endosome buffering and protecting DNA from lysosomal degradation.

To confirm and measure the damage induced by FGFR1 [TK-] transfection, standard methods can be used. For example, in vivo PET scanning can be used to assess the dopamine uptake sites in the striatum followed by postmortem striatal $^3$H-Mazindol binding measurement and HPLC catecholamine analysis. All animals can be PET scanned 10 days post-transfection, and some in each group can be sacrificed afterwards for the postmortem analysis. The other animals can be PET scanned as desired (such as after about day 30) and subsequently sacrificed for postmortem analyses.

The animal model generated by the method of the present invention can be used to study the degenerative changes which accompany PD. Further, this animal model can also be used for testing novel drugs and other therapeutic approaches to PD. For evaluation of potential therapeutic agents, the animals produced by the method described herein can be exposed to the test agents. The agents can be administered to the animal either by direct injection into the brain or via various routine methods of administration. The TH staining in animals at various times can be observed to identify any prophylactic or therapeutic effect.

EXAMPLE 1

This embodiment describes the injection of a TK deficient mutant of FGF1 into the SN of rats. The preparation and characteristics of this mutant are described in Peng et al. (Mol. Biol. Cell, 2001, 12:449–462, incorporated herein by reference). To illustrate this embodiment, a freshly prepared mixture of DNA construct with a final DNA concentration of about 0.4 $\mu$g/$\mu$l and linear 22 kDa PEI dissolved in 5% glucose is stereotaxically injected into SNc of anesthetized male Sprague-Dawley rats at a rate of 0.5 ml/min. The injection can be carried out into either the left or right SNc using stereotaxic coordinates: AP: –5.60 mm, ML: +/–1.5 mm., and DV: –8.2 mm. It was found that the most efficient transfection and longest-lasting expression (at least 2 months) were achieved by injecting SNc with 4 ml containing 1.5–3.0 mg of plasmid DNA and 6 PEI equivalents of DNA (one equivalence=amount of PEI required to neutralize the negative charges of DNA phosphate groups).

Figure 2:
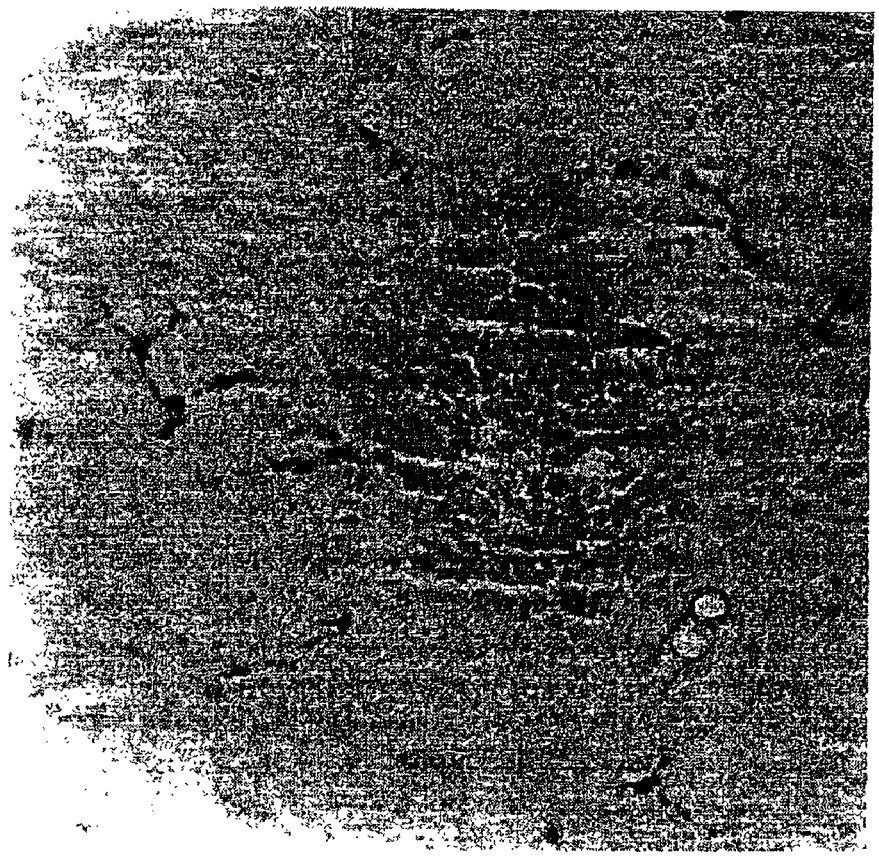
FIG. 2 is a photographic representation of PEI transfection of the substantia nigra with CMV β-gal.
Figure 3:
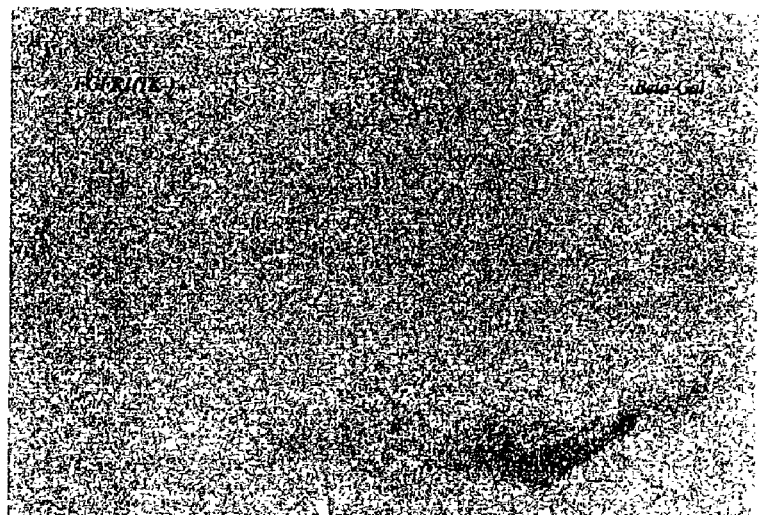
FIG. 3 is a photographic representation showing the loss of TH-positive neurons in rat SN four weeks after transfection of the TK deficient mutant. The control side was transfected with β-gal cDNA.
Figure 4:
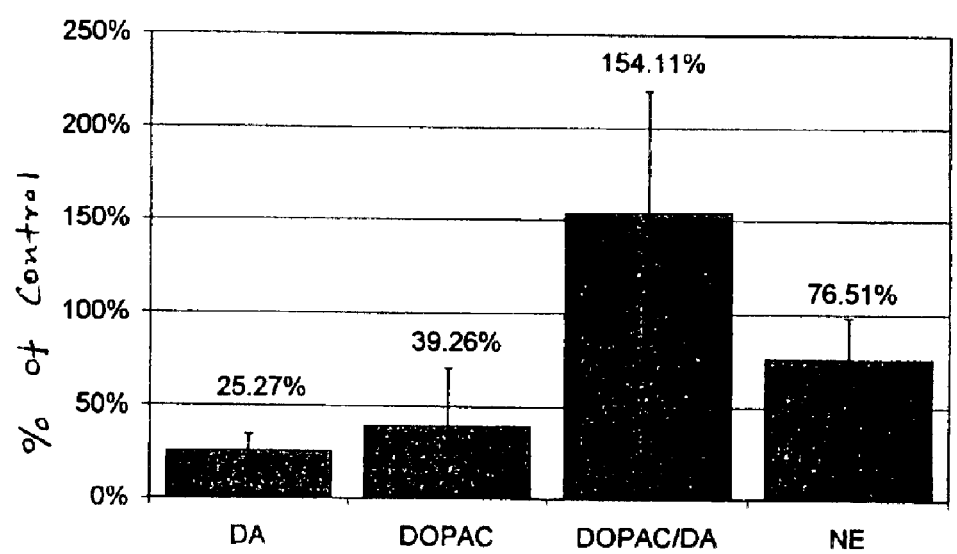
FIG. 4 is a representation of the striatal dompamine content following transfection with the TK deficient mutant.

Plasmids expressing β-gal or FGFR1[TK-] were injected stereotaxically into rat SNc. Expression of β-gal was detected using X-gal chemistry and DA neurons were stained with TH antibodies. The X-gal staining was observed in cells in the substantia nigra for at least 1 month after transfection (FIG. 2). Also, injection of FGFR1[TK-] was accompanied by a disappearance of TH positive neurons in the injected substantia nigra when examined 4–5 weeks after injection (FIG. 3) but not after 10–14 days (not shown). When β-gal was co-transfected with FGFR1[TK-] into the rat brain, β-gal activity was no longer detected 4 weeks after transfection. This could mean either a loss of expressing cells or an inhibition of the recombinant CMV-β-gal gene by FGFR1[TK-]. Since co-transfection FGFR1 [TK-] did not affect the short-term expression of β-gal, the loss of β-gal activity observed in vivo is likely to reflect the loss of expressing cells. Furthermore, the loss of TH-positive SNc neurons was accompanied by an 80% depletion of striatal DA (but not norepinephrine) suggesting degeneration of the dopaminergic terminals (FIG. 4). Thus, direct transfection into rat SNc with FGFR1[TK-] leads to a delayed (seen at 24–30 days, but not 10–14 days) near complete loss of TH immuno-positive neurons in SNc (FIG. 3). This is accompanied by an approximately 75% decrease in striatal DA content (FIG. 4). The delayed response seen in the present model is in contrast with the the observations with 6-OH dopamine or MPTP injected animals of the prior art. The delayed onset provides a greater opportunity for understanding the mechanisms underlying Parkinson's Disease and for identification of potential therapeutic agents.

To provide a control, in one embodiment, the animals can receive intranigral transfection of one of the FGFR1 expressing constructs into one randomly selected SNc side. The contralateral SNc will be transfected with a β-gal construct and will serve as the control. Many investigators have observed that there is no change in the DA content or turnover, DA synthesis, TH activity or mRNA levels contralateral to a unilateral 6-OHDA lesion, supporting the use of the side contralateral to FGFR1[TK-] injection as a control. However, since a small fraction of the SNc does project to the contralateral striatum, additional control animals can be used that receive a bilateral transfection of β-gal into the SNc. These β-gal/β-gal rats can be compared with the experimental FGFR1[TK-]/β-gal group to determine whether the nigro-striatal pathway on the β-gal-transfected side is affected by the transfection of FGFR1[TK-] into contralateral SNc.

EXAMPLE 2

To monitor the expression of the DNA constructs used to transfect cells, FGFR1[TK-]/βgal-transfected animals are anesthetized and perfused first with isotonic PBS (pH 7.2) then 4% paraformaldehyde fixative. Brains are removed, cryoprotected with 30% sucrose at 4° C., and then using a freezing stage microtome and systematically saving all sections are cut at about 5 mm thickness. Sections encompassing the SN can be immunostained for the human cMyc epitope (since the recombinant FGFR1 constructs have a C-terminal cMyc tag). Further, β-gal expression can be detected in alternative sections using anti-β-galactosidase Ab. The extent of cDNA transfection and expression can be determined using PCR (for DNA) and RT-PCR (for RNA). At each time point after transfection with FGFR1[TK-]/βgal, rats can be euthanized, the brains removed and the DNA and RNA extracted from dissected SN by grinding the tissue in 0.5 ml of Trizol TM. The DNA fraction can be used to determine the amount of transfected DNA present. The DNA is first measured by using PCR and primers specific for the recombinant β-galactosidase and FGFR1[TK-]Myc. Primers specific for rat actin can be used to standardize the amount of total DNA extracted. To determine the amounts of FGFR1[TK-]Myc and β-gal RNA's, the isolated RNA can be reversed transcribed using MoMuLV RT and random hexamer primers. Sensitivity of the PCR can be assessed by titrating specific amounts of the synthesized target RNA from the T3 promoter of a pcDNA3.1Myc/His plasmid containing either the FGFR1[TK-] or β-gal cDNA. Primers to the housekeeping gene adenosine phosphoribosyl transferase (APRT) can be employed to assess the relative amount of reverse-transcribable and amplifiable RNA in each sample. The PCR products can be resolved by electrophoresis, blotted to Nylon membrane and detected by hybridization with the appropriate cDNA probe. The β-gal FGFR1[TK-]Myc/His specific cDNA bands detected in this manner can be quantified by imaging on a Molecular Dynamics Phosphorimager.

The embodiments described herein are intended for the purpose of illustration and are not intended to be restrictive. Those skilled in the art will recognize that various modifications to the embodiments described herein can be made without departing from the spirit and scope of the invention.

What is claimed is:

1. A rodent model for a symptom of Parkinson's Disease comprising a rodent whose substantial nigra (SN) nucleus has been injected with a composition comprising a DNA sequence encoding a tyrosine kinase deficient mutant of fibroblast growth factor receptor-1 (FGFR1) and polyethyleneimine (PEI), wherein expression of the DNA sequence produces a tyrosine kinase deficient mutant that is a competitive antagonist of the wild type FGFR1 and wherein the dopamine content of the striatum is reduced when compared to control rodents.

2. The rodent model of claim 1, wherein a reduction in the dopamine content is observed after about 4 weeks.

3. The rodent model of claim 1, wherein the injection comprises 1.5 to 3.0 μg of plasmid DNA comprising said DNA sequence and about 6 PEI equivalents, wherein 1 PEI equivalent is the amount of PEI required to neutralize the negative charges of DNA phosphate groups in the plasmid DNA.

4. The rodent model of claim 1, wherein the injection is into the SN nucleus of one hemisphere.

5. The rodent model of claim 1, wherein a reporter gene operably linked to a promoter is also injected together with said DNA sequence.

6. The rodent model of claim 5, wherein the reporter gene encodes β-galactosidase.

7. A method for producing the rodent model of claim 1, comprising the steps of:
a) providing a rodent;
b) sterotaxically injecting a composition comprising a DNA sequence encoding a tyrosine kinase deficient mutant of FGFR1 and PEI into the SN nucleus of the rodent; and
c) expressing said DNA sequence,
wherein the dopamine content of the striatum is reduced when compared to control rodents.

8. The method of claim 7, wherein the injection comprises 1.5 to 3.0 μg of plasmid DNA comprising said DNA sequence and about 6 PEI equivalents, wherein 1 PEI equivalent is the amount of PEI required to neutralize the negative charges of DNA phosphate groups in the plasmid DNA.

9. The method of claim 7, wherein the injection is into the SN nucleus of one hemisphere.

10. The method of claim 9, wherein a reporter gene operably linked to a promoter is injected into the contralateral SN nucleus.

11. method of claim 7, wherein a reduction in the dopamine content of the SN nucleus is observed after about 4 weeks.

12. A method of evaluating the potential of an agent for treatment of Parkinson's disease comprising the steps of:
a) providing a rodent whose SN nucleus has been injected with a composition comprising a DNA sequence encoding a tyrosine kinase deficient mutant of FGFR1 and PEI, wherein expression of the DNA sequence produces a tyrosine kinase deficient mutant that is a competitive antagonist of the wild type FGFR1 and wherein the dopamine content of the striatum is reduced when compared to control rodents,
b) administering the test agent to said rodent;
c) comparing the dopamine content of the striatum with a control rodent; and
d) evaluating the effectiveness of the test agent based on change in the dopamine content of the striatum.

13. The method of claim 12, wherein the injection is into the SN nucleus of one hemisphere.

14. The method of claim 13, wherein a reporter gene operably linked to a promoter is injected into the contralateral SN nucleus.

15. The method of claim 12, wherein the injection comprises 1.5 to 3.0 μg of plasmid DNA comprising said DNA sequence and about 6 PEI equivalents, wherein 1 PEI equivalent is the amount of PEI required to neutralize the negative charges of DNA phosphate groups in the plasmid DNA.

* * * * *